US00PP29939P3

(12) United States Plant Patent
Ranney

(10) Patent No.: US PP29,939 P3
(45) Date of Patent: Dec. 4, 2018

(54) ***ILLICIUM* PLANT NAMED 'NCIH1'**

(50) Latin Name: *Illicium*
Varietal Denomination: NCIH1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 29 days.

(21) Appl. No.: 15/330,894

(22) Filed: Nov. 10, 2016

(65) Prior Publication Data
US 2018/0132401 P1 May 10, 2018

(51) Int. Cl.
*A01H 5/02* (2018.01)

(52) U.S. Cl.
USPC ..... Plt./226
CPC ..... *A01H 5/02* (2013.01)

(58) Field of Classification Search
USPC ..... Plt./226
See application file for complete search history.

*Primary Examiner* — Keith O. Robinson
(74) *Attorney, Agent, or Firm* — Myers Bigel, P.A.

(57) ABSTRACT

'NCIH1' is a new cultivar of hybrid *Illicium* with remontant flowering, a compact habit, and large, red flowers.

3 Drawing Sheets

Latin name of the genus and species: The Latin name of the novel plant variety disclosed herein is *Illicium*.

Variety denomination: The inventive hybrid of *Illicium* disclosed herein has been given the varietal denomination 'NCIH1'.

BACKGROUND OF THE INVENTION

The present invention comprises a new and distinct variety of *Illicium*, hereinafter referred to by the cultivar name 'NCIH1'. 'NCIH1' was selected from a population of seedlings grown from an open-pollinated, $F_1$ hybrid of *Illicium mexicanum* x *Illicium floridanum* (2004-318, unpatented). The first asexual propagation of 'NCIH1' was carried out in July 2007 by rooting stem cuttings in Mills River, N.C. and has been asexually reproduced repeatedly by vegetative cuttings over a 9-year period. 'NCIH1' roots readily from softwood and semi-hardwood cuttings treated with a basal dip of 5,000-10,000 ppm indole butyric acid (potassium salt) in water. Time to rooting for semi-hardwood cuttings is approximately 6 weeks at 30° C. 'NCIH1' has been found to retain its distinctive characteristics through successive asexual propagations.

SUMMARY OF THE INVENTION

The following are the unique combination of characteristics of this new cultivar when grown under standard horticultural practices in Mills River, N.C.

1. Remontant flowering: Primarily in the spring and fall and sporadically throughout the growing season.
2. A compact, upright habit.
3. Large, red flowers.

BRIEF DESCRIPTION OF THE DRAWINGS

This new *Illicium* is illustrated by the accompanying photographs which show the plant's flowers, foliage and form. The colors shown are as true as can be reasonably obtained by conventional photographic procedures. Colors in the photographs may differ slightly from the color values cited in the detailed botanical description, which accurately describe the colors of the new hybrid *Illicium*.

DETAILED BOTANICAL DESCRIPTION

Figure 1:
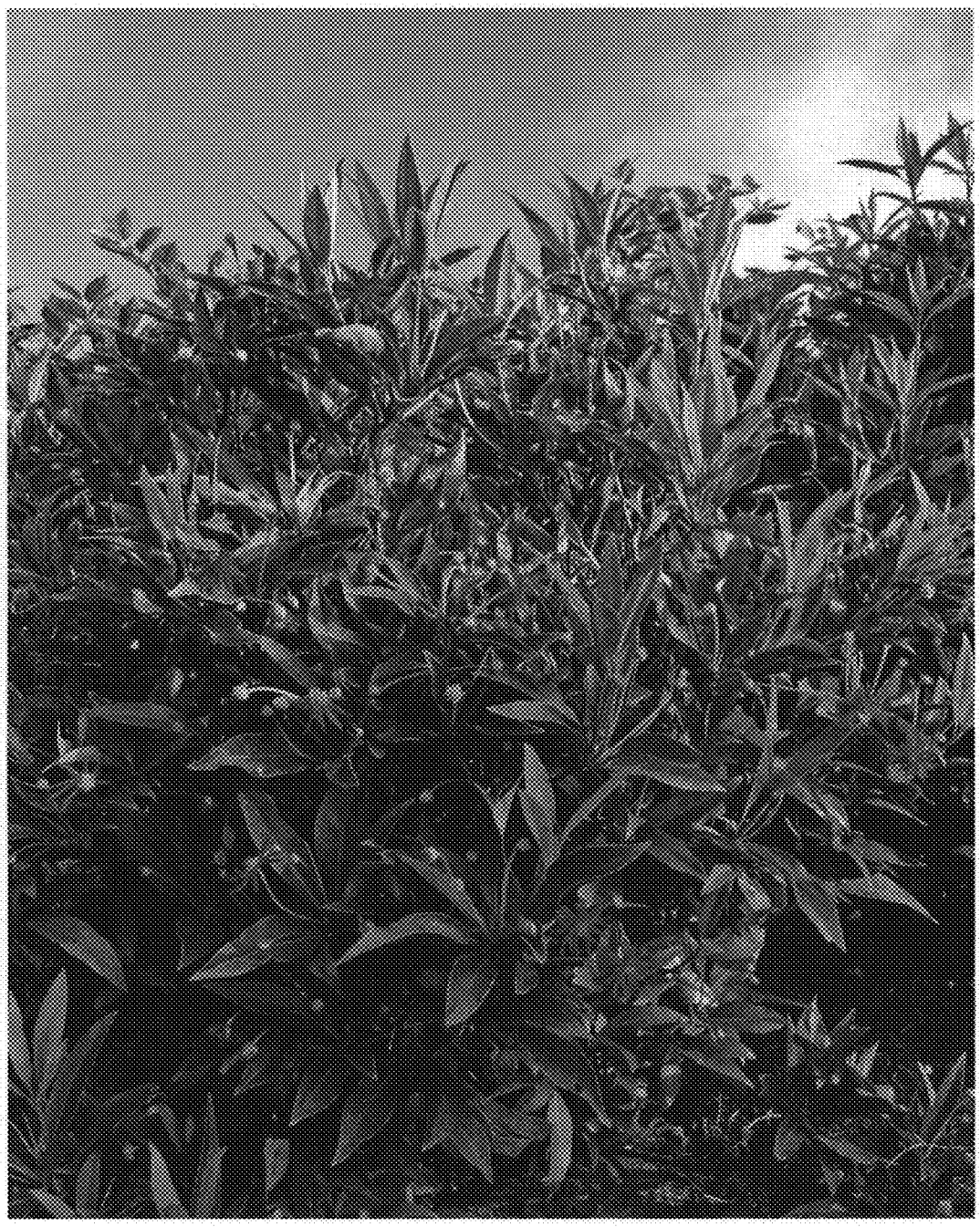
FIG. 1 is a photograph showing the compact habit and fall flowering of 'NCIH1' in September 2009 on a four-year-old field-grown shrub.
Figure 2:
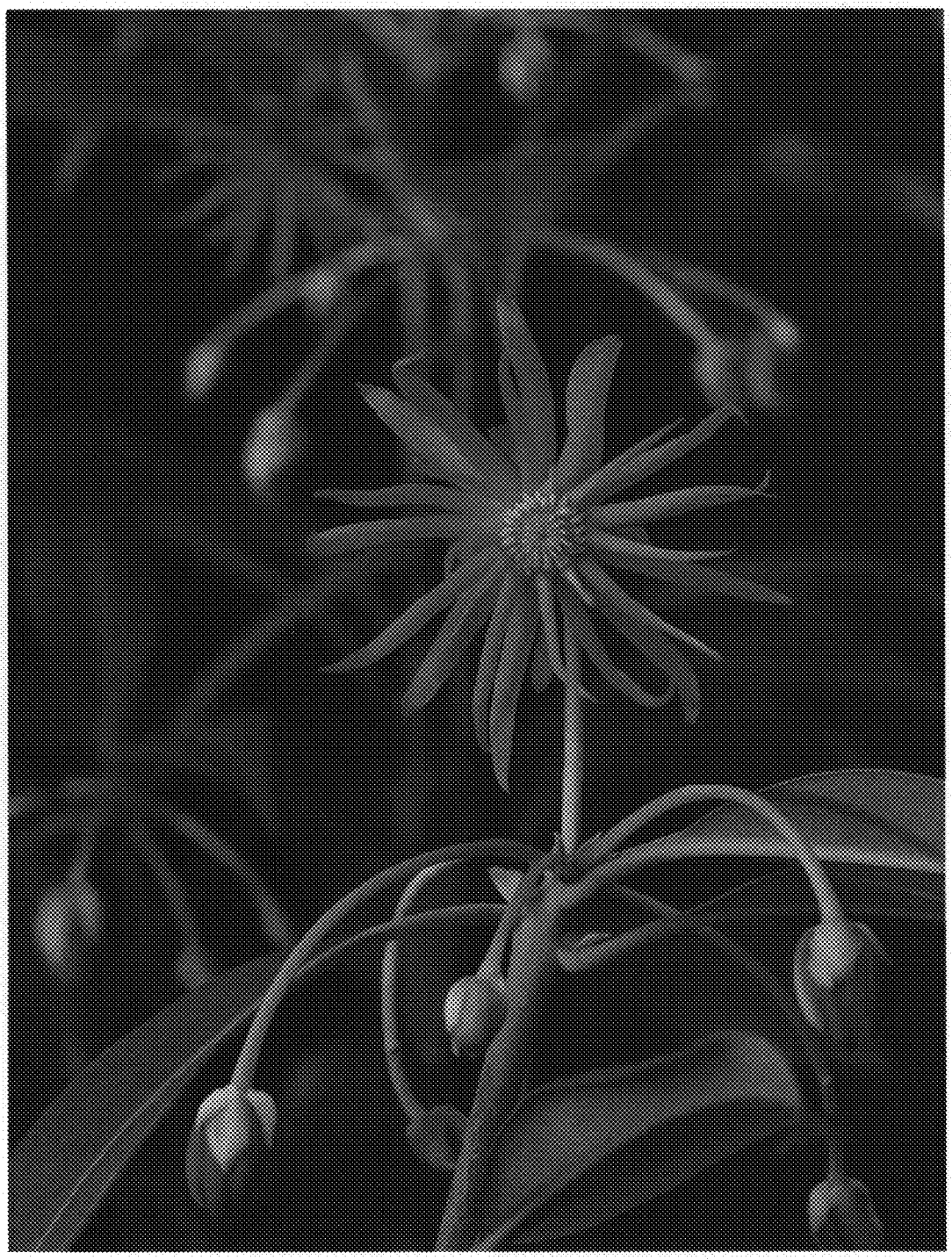
FIG. 2 is a photograph showing the flowers of 'NCIH1' in July 2013 on a three-year-old container-grown shrub.
Figure 3:
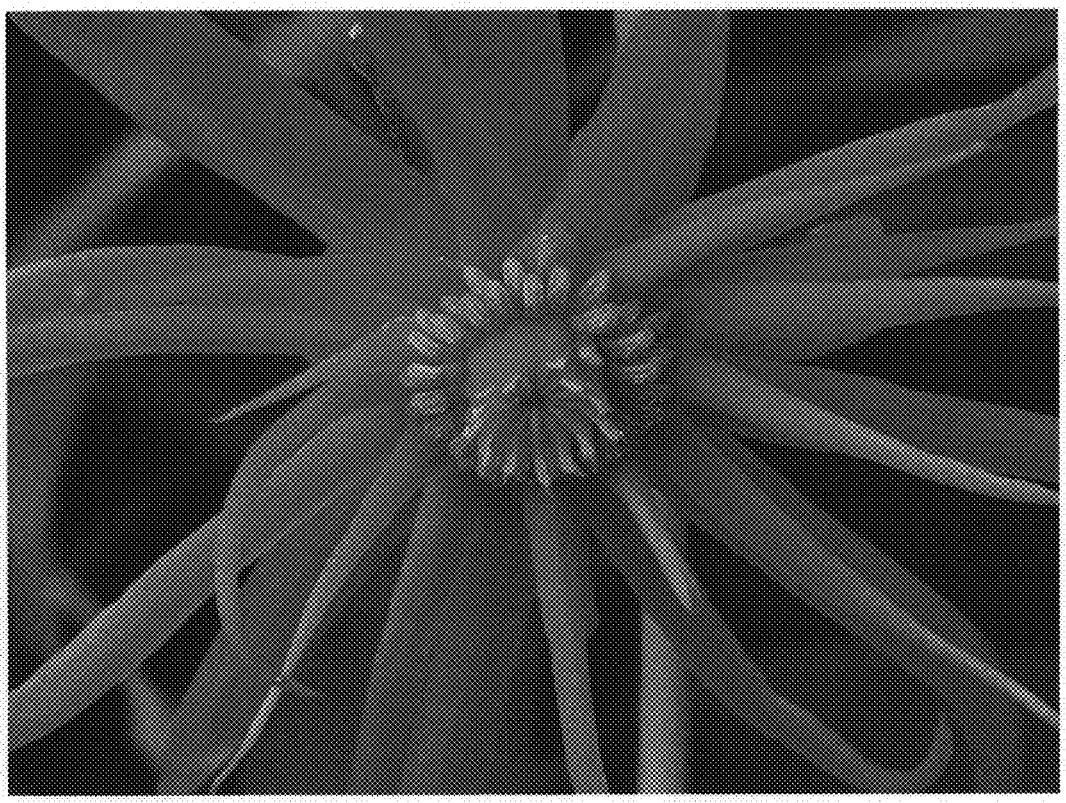
FIG. 3 is a photograph showing the flower morphology of 'NCIH1' in July 2013 on a three-year-old container-grown shrub.

The following is a detailed description of the botanical characteristics of the new and distinct hybrid *Illicium* variety plant known by the denomination 'NCIH1'. The detailed description was taken on a three-year-old field-grown plant in Mills River, N.C. in 2015. All colors cited herein refer to The Royal Horticultural Society (R.H.S.) Colour Chart, London, sixth edition, 2015. Where specific dimensions, sizes, colors, and other characteristics are given, it is to be understood that such characteristics are approximations or averages set forth as accurately as practicable.

TECHNICAL DESCRIPTION OF THE VARIETY

Classification:

*Botanical name.*—*Illicium* 'NCIH1'.

*Common name.*—Anise-shrub.

Parentage: Seedling grown from an open-pollinated, $F_1$ hybrid of *Illicium mexicanum* x *Illicium floridanum* (2004-318, unpatented).

Plant description:

*Growth habit.*—Upright, compact shrub.

*Height.*—Approximately 1.5 m at maturity.

*Width.*—Approximately 1 m at maturity.

*Growth rate.*—Moderate.

Shoot and stem:

*Lateral branch length*.—Avg. 30 cm (range 19 to 45 cm).

*Lateral branch diameter*.—Avg. 0.4 cm (0.3 to 0.6 cm).

*Branch characteristics*.—Moderate to dense branching, angled approximately 45-75°.

*Branch shape*.—Rounded to obovate.

*Internode length*.—Avg. 12.4 cm (4.8 to 20.5 cm).

*Texture*.—Glabrous.

*Immature shoot color*.—Yellow-green (146B).

*Mature stem color*.—Grey-brown (199A).

Leaves:

*Type*.—Simple.

*Aspect*.—leaf angled approximately 15-80° from lateral branches.

*Persistence*.—Evergreen.

*Arrangement*.—Alternate to pseudo-whorled.

*Shape*.—Elliptical.

*Apex*.—Acuminate.

*Base*.—Cuneate.

*Venation*.—Reticulate.

*Vein color*.—Upper: Yellow-green (144B). Lower: Yellow-green (144B).

*Margins*.—Entire.

*Emerging leaves*.—Color: Upper: Yellow-green (144A). Lower: Yellow-green (144A). Texture: Glabrous, shiny on both the upper and lower emerging leaves.

*Mature leaves during growing season*.—Color: Upper: Yellow-green (147A). Lower: Yellow-green (147B). Texture: Leathery, glabrous on both the upper and lower mature leaves. Length of lamina: Avg. 9.9 cm (6.8 to 11.6 cm). Width: Avg. 3.3 cm (2.5 to 3.5 cm).

*Foliage scent*.—Aromatic, anise-like.

*Leaf attachment*.—Petiolate.

*Petiole*.—Length: Avg. 1.2 cm (0.8 to 1.6 cm). Diameter: Avg. 0.2 cm (0.1 to 0.3 cm). Color: Yellow-Green (144B) darkening to Greyed-Red (180B). Texture: Glabrous.

Inflorescence:

*Flowering season*.—Two primary blooming periods; in April-May and again in September-November in Mills River, N.C. Flowers are also produced sporadically throughout the growing season.

*Arrangement*.—Single flowers, occurring at leaf axils, 1-6 flowers per axil.

*Lastingness of flowers*.—Approximately 5 to 10 days.

*Fragrance*.—Slight anise fragrance.

*Bud*.—Shape: Oblong. Texture: Glaborous. Length: Avg. 1 cm (0.7 to 1.3 cm). Diameter: Avg. 0.8 cm (0.7 to 1 cm). Color: Red-Purple (60A).

*Perianth*.—Diameter: Avg. 4.6 cm (4 to 7 cm). Height: Avg. 1.5 cm (1.2 to 1.8 cm).

*Perianth aspect*.—Outward facing to slightly nodding.

*Petals*.—Arrangement: Radial, slightly overlapping. Number: Avg. 25 (17 to 27). Texture, upper and lower surfaces: Smooth. Shape: Strap-shaped. Base: Truncate to rounded. Margin: Entire. Apex: Acute to acuminate. Length: Avg. 2.1 cm (1.2 to 2.5 cm). Width: Avg. 0.3 cm (0.2 to 0.5 cm). Color when opening: Upper: Red-Purple (60A). Lower: Red-Purple (60A). Color at maturity: Upper: Red-Purple (60A). Lower: Red-Purple (60A). Color fading to: Red-Purple (60A).

*Sepals*.—Shape: Oblong. Number: Avg. 3 (2 to 6 sepals). Margin: Entire. Apex: Obtuse. Base: Truncate to rounded. Color, mature: Upper: Red-Purple (60A). Lower: Red-Purple (60A), flushed with Yellow-Green (148A). Texture, upper and lower surfaces: Glabrous. Length: Avg. 1.1 cm (0.8 to 1.9 cm). Width: Avg. 0.5 cm (0.4 to 0.6 cm).

*Peduncle*.—Length: Avg. 2.4 cm (1.6 to 3.2 cm). Diameter: Avg. 0.20 cm (0.15 to 0.25 cm). Color: Yellow-Green (144C). Surface texture: Glabrous.

Reproductive organs:

*Gynoecium*.—Pistil number: 1 aggregate of 9-14 pistils. Pistil length: 0.5 cm. Style length: 0.2 cm. Style color: Yellow-Green (145C).

*Androecium*.—Stamen number: 12 to 36. Stamen length: 0.2 cm. Stamen width: 0.1 cm. Stamen color: Greyed-Purple (185D). Pollen color: White (155B). Pollen abundance: Moderate.

Fruit and seed:

*Fruit type*.—Star-shaped, woody follicetum.

*Fruit diameter*.—Avg. 2.3 cm (2 to 2.8 cm).

*Fruit color*.—Immature: Yellow-Green (N144A). Mature: Brown (N200A).

*Seed number*.—Avg. 13 (9 to 14) per fruit.

*Seed size*.—Length: Avg. 0.8 cm (0.6 to 0.9 cm). Width: Avg. 0.4 cm (0.3 to 0.5 cm).

Roots: Soft, fibrous young roots, woody older roots (greyed-brown, RHS 199D).

Disease and insect resistance: No significant disease or insect pests have been observed.

Cold hardiness: At east USDA zone 6a; testing has not been completed in colder zones.

COMPARISON WITH COMMERCIAL CULTIVARS

Table 1 shows distinguishing characteristics between 'NCIH1' and other *Illicium* cultivars. 'NCIH1' is distinguished from *Illicium* 'Woodland Ruby' by having a more compact habit, redder flowers, and more remontant flowering. 'NCIH1' is distinguished from *Illicium* 'NCIH2' (Plant patent application Ser. No. 15/330,892) in that 'NCIH1' has red flowers and 'NCIH2' has white flowers.

TABLE 1

Comparison to commercial cultivars.

| | Taxa | | |
|---|---|---|---|
| Trait | *Illicium* 'Woodland Ruby' (unpatented) | *Illicium* 'NCIH1' | *Illicium* 'NCIH2' |
| Flowering season | Mostly April-May | Remontant. Mostly in April-May and September-November | Remontant. Mostly in April-May and September-November |
| Plant habit and size | Upright to 2 m tall and 1.5 m wide | Upright to 1.5 m tall and 1 m wide | Upright to 1.5 m tall and 1 m wide |
| Branch length | Avg. 62 cm | Avg. 30 cm | Avg. 29 cm |
| Petal color | Purplish Pink (RHS 63C to 67C) | Red-Purple (RHS 60A) | Yellowish-White (RHS NN155A) |
| Leaf length | Avg. 10.6 cm | Avg. 9.9 cm | Avg. 12.3 cm |

COMPARISON WITH FEMALE PARENT

*Illicium* 'NCIH1' is distinguished from its open-pollinated, female parent 2004-318, in that 'NCIH1' has red flowers, remontant flowering, and a compact habit, while 2004-318 has pink flowers (RHS 64C), does not have remontant flowering, and is much larger growing, exceeding 2M tall.

What is claimed:

1. A new and distinct hybrid *Illicium* plant named 'NCIH1' substantially as illustrated and described herein.

* * * * *